United States Patent [19]

Pascarella et al.

[11] Patent Number: 5,326,366
[45] Date of Patent: Jul. 5, 1994

[54] BIOMECHANICAL GREAT TOE IMPLANT

[75] Inventors: Joanne M. Pascarella, Memphis, Tenn.; John V. Vanore, Burr Ridge, Ill.

[73] Assignee: Wright Medical Technology, Inc., Arlington, Tenn.

[21] Appl. No.: 17,569

[22] Filed: Feb. 16, 1993

[51] Int. Cl.$^5$ ............................................. A61F 2/42
[52] U.S. Cl. ................................... 623/21; 623/18
[58] Field of Search ..................... 623/18, 21, 20, 16

[56] References Cited

U.S. PATENT DOCUMENTS

| | | | |
|---|---|---|---|
| 3,891,998 | 7/1975 | Lennox | 623/18 |
| 4,156,296 | 5/1979 | Johnson et al. | 623/21 |
| 4,634,444 | 1/1987 | Noiles | 623/20 |
| 4,642,122 | 2/1987 | Steffee | 623/21 |
| 4,645,505 | 2/1987 | Swanson | 623/18 |
| 4,685,919 | 8/1987 | Niwa et al. | 623/18 |
| 4,731,087 | 3/1988 | Sculco et al. | 623/21 |
| 4,769,039 | 9/1988 | Horber | 623/20 |
| 4,908,031 | 3/1990 | Frisch | 623/21 |
| 5,011,496 | 4/1991 | Forte et al. | 623/20 |
| 5,037,440 | 8/1991 | Koenig | 623/21 |
| 5,047,059 | 9/1991 | Saffar | 623/21 |
| 5,116,375 | 5/1992 | Hofmann | 623/20 |
| 5,137,536 | 8/1992 | Koshino | 623/20 |

FOREIGN PATENT DOCUMENTS

| | | | |
|---|---|---|---|
| 0198586 | 10/1986 | European Pat. Off. | 623/21 |
| 2605878 | 5/1988 | France | 623/21 |
| 2645735 | 10/1990 | France | 623/21 |
| 2651119 | 3/1991 | France | 623/21 |

Primary Examiner—Randall L. Green
Assistant Examiner—D. Willse

[57] ABSTRACT

A prosthetic implant for resurfacing a damaged base portion of the proximal phalanx in a human great toe comprises a base fabricated from a titanium, ceramic or other durable and rigid biocompatible material. The base is generally elliptical and includes an anatomically-shaped proximal articular surface having an enlarged build-up on the lateral end thereof. The base also includes a generally planar distal seating surface disposed for engaging the sectioned portion of the proximal phalanx. An elongated stem extends distally from the seating surface of the base and includes an array of fins together having a cruciate-shaped cross section. The fins each include a plurality of serrations along their sloping edges for anchoring the stem within the cancellous portion of the proximal phalanx.

4 Claims, 2 Drawing Sheets

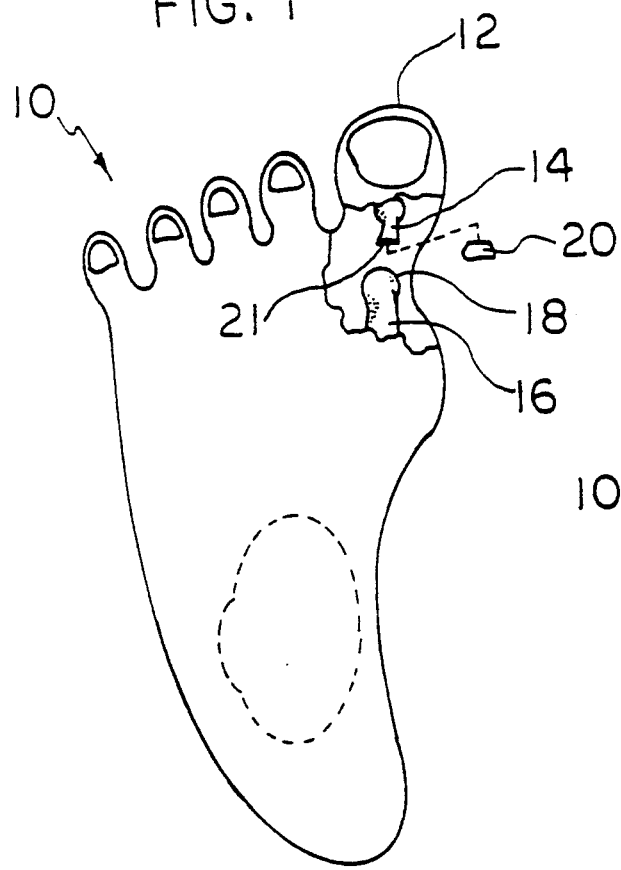
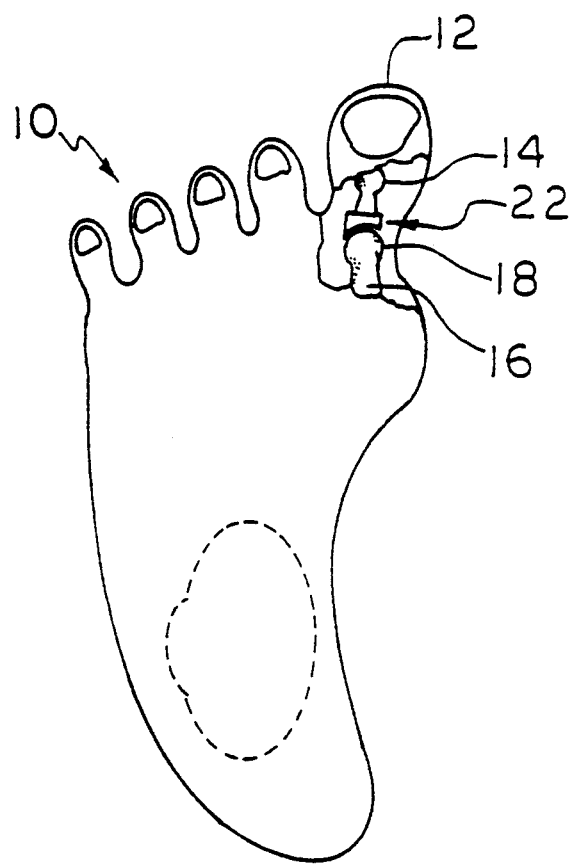

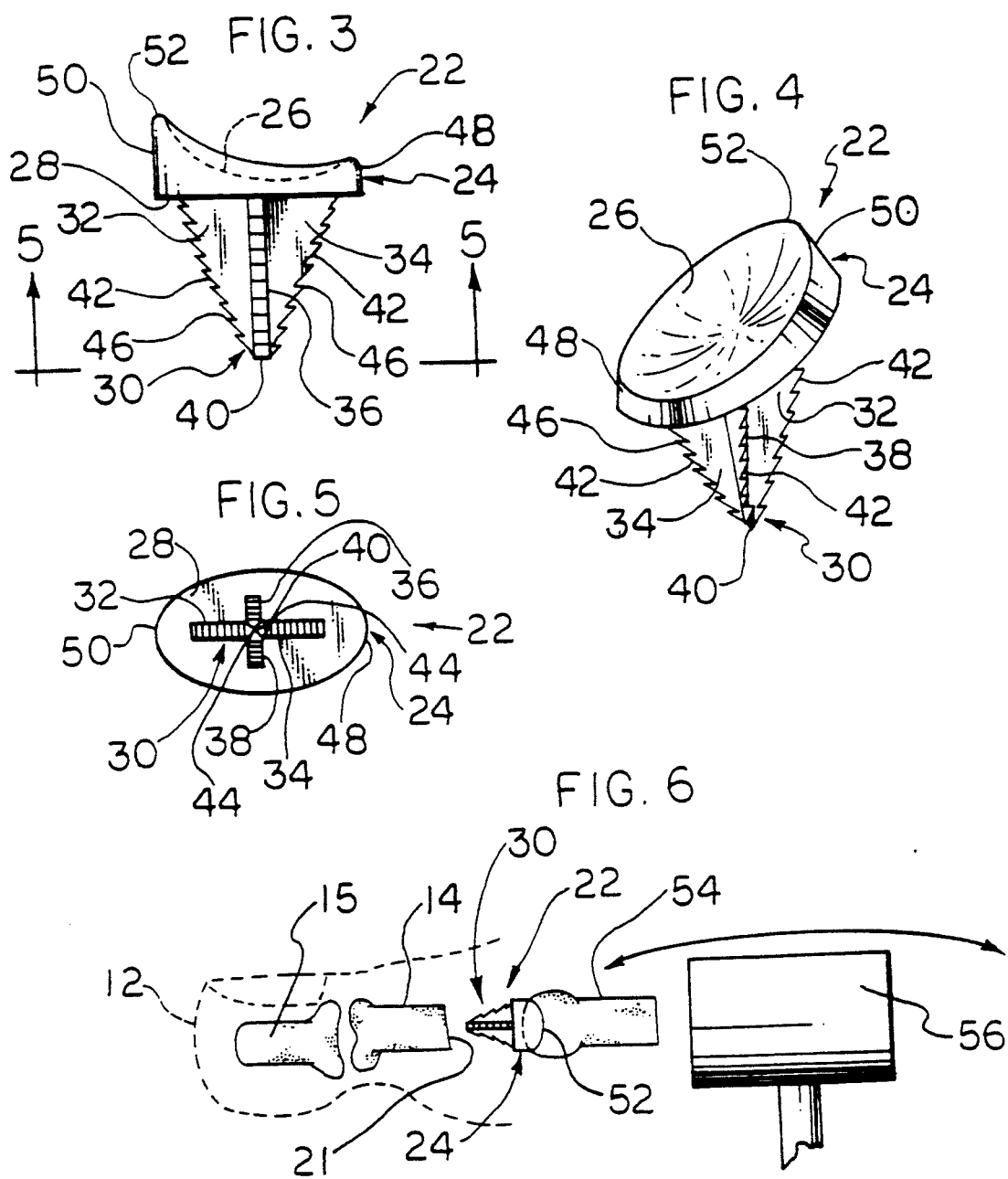

BIOMECHANICAL GREAT TOE IMPLANT

TECHNICAL FIELD

The subject invention relates generally to hemiarthroplasty of small orthopedic joints, and particularly to resurfacing a damaged base portion of a proximal phalanx with an implant for a human great toe.

BACKGROUND ART

Many people suffer from discomfort caused by damaged articular surfaces between the proximal phalanx and the first metatarsal caused by either rheumatoid arthritis, osteoarthritis or trauma to that portion of the foot. Such discomfort is often aggravated and sometimes precipitated, by frequently wearing pointed-toe ladies' dress shoes or cowboy boots. These pointed-toe shoes apply medial-lateral forces to the big, or great, toe, degrading the lateral head of the first metatarsal.

The prior art has taught prosthetically resurfacing the proximal phalanx using a medical implant having a button-like base and a square or rectangular stem extending downwardly therefrom. Examples of such prior art implants include the Swanson SILASTIC TM great toe implant and the Swanson Titanium great toe implant, both manufactured by Dow Corning Wright, 5677 Airline Road, Arlington, Tenn. 38002. The base includes either a flat or simple concave proximal articular surface for articulating with the head of the first metatarsal. A generally planar distal seating surface is provided, opposite the articular surface of the base, for seating against the sectioned portion of the proximal phalanx. A square or rectangular hole is formed in the proximal phalanx during surgery to receive the mating stem of the implant.

The primary deficiency of the prior art proximal phalanx implant is that the proximal articular surface is not shaped to approximate the anatomical convex surface curvature of the head of the first metatarsal, thereby resulting in uneven, tangential contact and increased wear between the implant and the head of the first metatarsal. This increased wear generates particulate debris which contributes to premature failure of the implant. Additionally, use of the square or rectangular stem is less conservative of bone, i.e., requiring significant cancellous portions of the proximal phalanx to be removed, thereby considerably disturbing endosteal blood supply in the proximal phalanx.

The subject invention is directed toward an implant which more naturally articulates with the head of the first metatarsal, provides an extended useful life, causes minimal disturbance to the cancellous portion of the first metatarsal, and is easily implanted during surgery.

SUMMARY OF THE INVENTION AND ADVANTAGES

The subject invention provides a medical implant for resurfacing a damaged based portion of the proximal phalanx in a human big toe. The implant comprises a base having a proximal articular surface shaped to articulate with the head of a human first metatarsal having a generally planar distal seating surface opposite the articular surface. A stem extends distally from the seating surface for anchoring the implant in a cancellous portion of the proximal phalanx. A plurality of fins each having pointed leading ends are arranged about the stem and minimize disturbance of endosteal blood supply in the proximal phalanx with improved conservation of bone.

According to another aspect of the invention, the articular surface has a concave surface curvature for complementing the anatomical convex surface curvature of the head of the proximal phalanx and thereby naturally articulating with the head of the first metatarsal.

An advantage of the subject invention is that the concave surface curvature of the articulating surface of the implant better contacts with the head of the first metatarsal, reducing the generation of wear particles in the joint, and further extending the useful life of the implant.

Another advantage of this invention is that the plurality of fins on the stem sufficiently anchors the implant in the proximal phalanx so as to prevent rotation and translation, causing minimal damage to the surrounding cancellous portion of the proximal phalanx while occupying a limited volume therein.

A further advantage of the invention is that the endosteal blood supply is not significantly disrupted.

A still further advantage is that the subject implant is easily and quickly installed during surgery.

BRIEF DESCRIPTION OF THE DRAWINGS

Other advantages of the present invention will be readily appreciated as the same becomes better understood by reference to the following Detailed Description when considered in connection with the accompanying Drawings wherein:

FIG. 1 is a dorsal view of a human foot showing in partial section the proximal phalanx and first metatarsal, where the base portion of the proximal phalanx has been surgically resected;

FIG. 2 is a view as in FIG. 1, showing the subject implant disposed in operative position on the proximal phalanx;

FIG. 3 is a front elevation view of the subject implant;

FIG. 4 is a perspective view of the subject implant;

FIG. 5 is a bottom view of the subject implant looking proximally toward the operative joint of FIG. 3; and FIG. 6 is a simplified view showing surgical installation of the implant using a setting tap and striking mallet.

DETAILED DESCRIPTION OF THE PREFERRED EMBODIMENT

Referring to the Figures, wherein like numerals indicate like or corresponding parts throughout the several views, the human left foot is generally shown at 10 in FIGS. 1 and 2. The foot 10 includes a plurality of phalanges including a big toe 12. The two bones in the big toe 12 comprises a proximal phalanx 14 disposed for operative articulation with a first metatarsal 16, and a distal phalanx 15 (FIG. 6). The first metatarsal 16 includes a head portion 18.

As best shown in FIG. 1, the proximal phalanx 14 includes a base portion 20 (anatomical position shown by broken line) which is often damaged by osteoarthritis, trauma, etc, thus requiring excision as shown. In typical fashion, a sagittal saw or other cutting instrument is used to shave the base portion 20 from the proximal phalanx 14, leaving a generally planar resected proximal surface 21. Referring to FIG. 2, the damaged base portion 20 of the proximal phalanx 14 is shown surgically replaced by the distinctive prosthetic medical implant of the subject invention, generally shown at 22. The implant 22 replaces the damaged base portion 20 and articulates with the head 18 of the first metatarsal 16 in a natural and comfortable manner.

Referring to FIGS. 3-5, the implant 22 is shown including a base, generally indicated at 24 which structurally fills the gap left by the resected base portion 20 of the proximal phalanx 14. The base 24 of the implant 22 is preferably fabricated from titanium, ceramic, or some other durable and biocompatible material. The base 24 includes a proximal articular surface 26 configured to articulate with the correspondingly-shaped head 18 of the first metatarsal 16, as shown in FIGS. 2 and 6. The base 24 also has a generally planar distal seating surface 28 disposed opposite the articular surface 26, which impinges on the resected proximal surface 21 of the proximal phalanx 14.

The implant 22 is sized to take-up space left by the resected base 20 while providing smooth articulation. Whereas the prior art implants are essentially nothing more the spacers, the subject implant 22 has a complex concave surface curvature which is complementary to the anatomical convex surface curvature of the natural head 18 of the first metatarsal 16.

An elongated stem generally indicated at 30, extends perpendicularly from the seating surface 28 and is received within the cancellous portion for anchoring the implant 22 to the proximal phalanx 14. More specifically, the stem 30 includes a plurality of generally triangular fins 32, 34, 36, 38 each having pointed leading ends 40 and all arranged to minimize disturbance of endosteal blood supply in the proximal phalanx 14. The pointed leading ends 40 converge to form an apex as shown, e.g., in FIGS. 3 and 4. Each of the fins 32, 34, 36, 38 are shaped of a right triangle configuration having one sloping edge 42 oblique to the planar seating surface 28 and a common perpendicular edge 44 merged with each of the other fins. In other words, the sloping edges 42 of the fins 32-38 form the hypotenuse of their triangular configuration.

To enhance fixation of the implant 22 in the proximal phalanx 14, the sloping edges 42 of each of the fins 32-38 are provided with a plurality of serrations 46 formed therealong. As best shown in FIG. 3, the serrations are in the form of barbs each having a slight proximal cant which provides for easy insertion, yet resists removal from the cancellous portion of the proximal phalanx 14. And, as most evident in FIG. 5, the orientation of the fins 32-38 forms a cruciate configuration, with each fin arranged in a plane perpendicular to the next adjacent fins. In other words, the fins are arranged in a generally X-shaped formation which provides maximum anchorage in the proximal phalanx 14, while preventing rotation of the implant 22 relative to the proximal phalanx 14 and minimal disturbance of the endosteal blood supply therein.

Referring again to FIGS. 3 and 4, the articular surface 26 of the base 24 has a complex concave surface curvature the anatomical convex surface curvature of the natural head 18 of the first metatarsal 16. In other words, the articular surface 26 is dished for conforming to the anatomically convex head 18 of the first metatarsal 16. Hence, the implant 22 provides a functional advantage over the prior art implants by increasing surface contact between the articulating members and consequentially reducing localized loading between the implant 22 and the first metatarsal 16.

The articular surface 26 includes a medial side 48 and a lateral side 50. The convex surface curvature of the articular surface 26 is biased somewhat to the medial side 48, so as to form a build-up 52 that extends upwardly from the articular surface 26 along the lateral side 50. The build-up 52 provides an extended engagement surface with the head 18 of the first metatarsal 16 where the lateral side of the head 18 is abraded in a manner typically caused by pointed shoes, as described above. Thus, the lateral build-up 52 on the articular surface 26 very closely approximates the actual anatomical convex surface curvature of the head 18 of the first metatarsal 16 and constrains natural forces applied as a result of the above motion.

To this end, the base 24 of the implant 22 is formed having a generally elliptical perimeter, as best shown in FIGS. 4 and 5, with an imaginary major axis aligned with the medial 48 and lateral 50 sides, and a shorter and perpendicular imaginary minor axis. Thus, the peripheral dimension as measured between the medial 48 and lateral 50 sides is slightly larger than the outer dimension as measured in an anterior/superior direction. Although various sizes of the implant 22 are required to accommodate the varying anatomical sizes of patients, one such implant size includes a base 24 having a peripheral dimension measured along the imaginary major axis of about 0.710 inches and a peripheral dimension measured along the imaginary minor axis of about 0.590 inches. The same implant would include a lateral build-up 52 dimension measured from the highest point to the seating surface 28 of about 0.262 inches and a convex surface curvature radius of approximately 0.560 inches.

Referring again to the stem 30, the configuration of the cruciate fins 32-38 is preferably arranged to comprise a pair of medial/lateral fins 32, 34 and a pair of inferior/superior fins 36, 38 perpendicular to the pair of medial/lateral fins 32, 34. Therefore, as shown in FIG. 5, the medial/lateral fins 32, 34 extend horizontally and the inferior/superior fins 36, 38 extend vertically. Or, said another way, the medial/lateral fins 32, 34 are aligned along the major axis of the elliptical base 24, and the inferior/superior fins 36, 38 are aligned along the minor axis. According to this arrangement, it is preferable that the included angle between the sloping edges 42 of the medial/lateral fins 32, 34 be greater than the included angle between the sloping edges 42 of the inferior/superior fins 36, 38. More specifically, and referring again to the exemplary dimensions of the implant 22 referenced above, it is found that in included angle between the sloping edges 42 of the medial/lateral fins 32, 34 is preferably about 48°, whereas the included angle between the sloping edges 42 of the inferior/superior fins 36, 38 is preferably about 39°. Of course, other angles and other fin configurations are possible. Further, it has been found that the thickness of the fins 32, 34, 36, 38 is preferably about 0.065 inches.

The subject implant 22 is installed during surgery by first sectioning the base 20 of the proximal phalanx 14, such as with a sagittal saw or other medical cutting instrument, to form a smooth, planar receiving surface for the implant 22. It is preferably that the smallest possible section of the base 20 be removed such that the soft cancellous inner portion of the proximal phalanx 14 may or may not be revealed.

Once the base 20 of the proximal phalanx 14 has been properly sectioned and removed, as shown in FIG. 1, the subject implant 22 is positioned so that the pointed leading end 40 of the stem means 30 is centered on the freshly sectioned receiving surface of the proximal phalanx 14, as illustrated in FIG. 6. The implant 22 is arranged so that the medial side 48 and lateral side 50 of the articular surface 26 is coordinated with the patient's foot 10. Once properly positioned, the implant 22 is seated in the proximal phalanx 14 by forcibly driving the stem means 30 into the cancellous portion of the proximal phalanx 14. To aid insertion, a setting tap 54 is specially formed to engage the articular surface 26 of the implant 22. The tap 54 is struck repeatedly with a mallet 56 until the stem means 30 is driven fully into the proximal phalanx 14 and the seating surface 28 is brought into surface-to-surface engagement with the freshly sectioned receiving surface of the proximal phalanx 14.

With this, the serrations 46 on the fins 32, 34, 36, 38 engage and grip within the cancellous inner portion of the proximal phalanx 14 to securely grip and retain the implant 22 in position to articulate with the head 18 of the first metatarsal 16. Surgical procedures are then implemented to close the wound in the patient's foot 10.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

What is claimed is:

1. A medical implant for resurfacing a damaged base portion of a proximal phalanx in a human great toe, said proximal phalanx having a cancellous interior portion, the implant comprising:
   (1) a base having
      a concave proximal articular surface shaped to naturally articulate with a head of a human first metatarsal, and
      a generally planar distal seating surface opposite the articular surface;
   (2) said articular surface defining a medial side and a lateral side and including a build-up extending upwardly from the distal seating surface along the lateral side;
   (3) a stem extending perpendicularly from the seating surface of the base for anchoring the implant in the cancellous portion of the proximal phalanx;
   (4) the stem including a plurality of fins arranged in a cruciate configuration;
   (5) each of said fins having a triangular configuration which defines pointed leading ends and one sloping edge oblique to the planar seating surface; and
   (6) each of said sloping edges having a plurality of serrations formed therealong.

2. An implant as set forth in claim 1 wherein said fins comprise: a pair of medial/lateral fins and a pair of inferior/superior fins perpendicular to the pair of medial/lateral fins; the sloping edges of each pair of fins defining an included angle; and the included angle defined by the sloping edges of the medial/lateral fins being greater than the included angle defined by the sloping edges of the inferior/superior fins.

3. A medical implant for resurfacing a damaged base portion of a proximal phalanx in a human great toe, said proximal phalanx having a cancellous interior portion, said implant being adapted for articular engagement with a head of a human first metatarsal, said head of said first metatarsal defining an anatomical convex curvature, said implant comprising:
   (1) a base having
      a concave proximal articular surface shaped to naturally articulate with the head of said human first metatarsal, and
      a generally planar distal seating surface opposite the articular surface;
   (2) said articular surface defining a medial side and a lateral side and including a build-up extending upwardly from the distal seating surface along the lateral side;
   (3) a stem extending perpendicularly from the seating surface of the base for anchoring the implant in the cancellous portion of the proximal phalanx; and
   (4) said concave articular surface complementing said anatomical convex curvature of said first metatarsal head.

4. An implant as set forth in claim 3 wherein: the base has a generally elliptical perimeter defining a major axis and a minor axis; and said medial and lateral sides are aligned with said major axis.

* * * * *